United States Patent [19]
Ai et al.

[11] Patent Number: 4,795,345
[45] Date of Patent: Jan. 3, 1989

[54] ARTIFICIAL TEETH

[75] Inventors: Minoru Ai, Tokyo; Kenji Hiranuma, Nagoya; Jinichi Obana, Tokyo; Toshio Ito, Kasugai, all of Japan

[73] Assignee: G-C Toshi Kogyo Corporation, Kasugai, Japan

[21] Appl. No.: 105,723

[22] Filed: Oct. 7, 1987

[30] Foreign Application Priority Data

Oct. 31, 1986 [JP] Japan .............................. 61-258478

[51] Int. Cl.$^4$ .............................................. A61C 13/08
[52] U.S. Cl. .................................. 433/202.1; 433/192; 433/218
[58] Field of Search .................. 433/202.1, 206, 212.1, 433/218, 192, 197, 198

[56] References Cited

U.S. PATENT DOCUMENTS

| | | | |
|---|---|---|---|
| 178,143 | 5/1876 | Hall ...................................... | 433/192 |
| 1,743,873 | 1/1930 | Zaslove ................................ | 433/192 |
| 2,419,084 | 4/1947 | Myerson et al. ................... | 433/212.1 |
| 2,585,857 | 2/1952 | Schwartz ............................. | 433/206 |
| 3,468,028 | 9/1969 | Sunter ................................. | 433/218 |

*Primary Examiner*—John J. Wilson
*Attorney, Agent, or Firm*—Oblon, Fisher, Spivak, McClelland & Maier

[57] ABSTRACT

An artificial tooth has a length of its buccal side substantially equal to that of a natural tooth and a length of its lingual side in the range of 4.0 mm to a length shorter than the length of its buccal side by at least 2.5 mm. A basal surface is of a concave shape in engagement with a more convex shape than the shape in cross-section of the alveolar ridge. One or two proximal surfaces of the basal surface is or are provided at the substantial center with an occlusally inclined smooth groove having a width of 1.5 to 5.0 mm, a maximum depth of 0.5 to 3.0 mm, and an proximal upper end located away from the highest position. The occlusal surface has a mesiodistal length substantially equal to that of a natural tooth and a $W_2/W_1$ ratio falling in the range of 55 to 95% of that of a natural tooth, wherein $W_1$ is the mesiodistal length and $W_2$ is the buccolingual length.

4 Claims, 2 Drawing Sheets

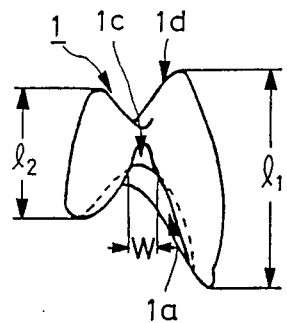
FIG. 5
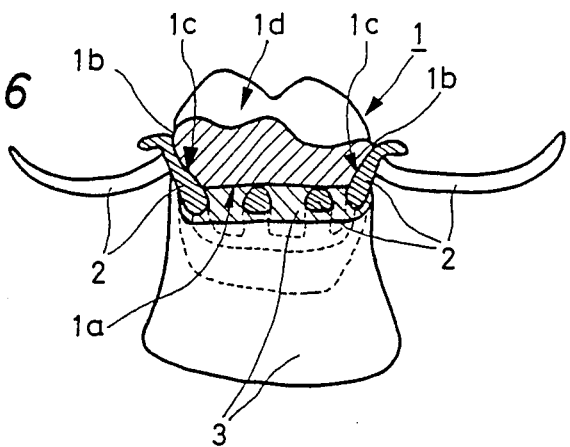
FIG. 6
FIG. 7
PRIOR ART

ARTIFICIAL TEETH

BACKGROUND OF THE INVENTION

1. Field of the Invention

The present invention relates to an artifical tooth which is formed of a porcelain or synthetic resin material. The artifical tooth is particularly designed for a molar tooth suitable for the preparation of a partial denture.

2. Background of the Invention

In dentistry, a full or partial denture has been put in the mouth for making up for a full or partial loss of teeth with a view to recovering the appearance or the decline of functions (such as mastification and pronunciation) resulting from such a loss.

In particular, partial dentures are most frequently used to cover a variety of cases from a loss of one tooth to the presence of one tooth left. In general, such partial dentures compose a retainer, a connector, a denture plate, and an artifical tooth or teeth. When preparing the partial dentures, attention should be paid to biological particulars in the design of the retainer and the connector. In the selection and alignment of artificial teeth, attention also has to be paid to the appearance thereof and to the recovery of functions (such as mastification and pronunciation). In the selection and alignment of artifical teeth, therefore, special regard must be paid to the size, form, color tone, vertical height, location, proximal consideration, occlusal consideration, and so on of the artifical teeth, depending upon the state of the remaining tooth or teeth.

However, since the conventional artifical teeth have usually been designed and made with full dentures in view, suitable artificial teeth selected from such teeth made for full dentures have been used to make partial dentures. As illustrated in FIG. 7, one of the conventional artifical teeth designed for use with full dentures is slightly bent in the buccolingual direction. Hence, this tooth should be used in combination with a retainer, a connector, and a metal plate, when preparing a partial denture. In this case, it is inevitably required that the basal and proximal surfaces of the tooth be partly removed by cutting. As a result, not only is much time required for the preparation of a partial denture, but the contour and appearance of the artifical tooth are deteriorated. This operation thus gives an operator a great deal of trouble.

To solve such a problem, Japanese Utility Model Publication No. 37-2475 proposes an artifical tooth for the preparation of a partial denture, which has its basal surface provided at the center with a concave dent. According to the teachings disclosed therein, the proximal surface adjacent to that concave dent is formed with an elongate retaining groove extending from the bottom of the basal surface thereof, and a small dent of a relatively large size is formed above the groove for the insertion of a retainer.

However, the artificial tooth disclosed in Japanese Utility Model Publication No. 37-2475 is formed so that its basal surface is only provided at its center with the concave dent, and it has a contour similar to that of an ordinary natural tooth except for the elongate retaining groove extending from the bottom of the basal surface of the proximal surface and the small dent of a relatively large size formed above the groove. Hence, the retainer, the connector, and the projections from the metal plate are often located below the lingual side of the artificial tooth. In many cases, therefore, the lingual lower portion of the artificial tooth must be removed by cutting to a large extent. With this artificial tooth, a significant reduction in the amount of operation to be conducted by an operator is still not achieved. Besides, a denture having a sufficient stable strength still cannot be prepared, since a synthetic resin-made dental plate cannot be firmly filled in the central concave dent due to the fact that the central concave dent in the basal surface is, for the most part, surrounded by the side walls of the artificial tooth.

Further, this known artificial tooth offers problems in connection with stability and a wearer's load, when used as a partial denture, on the lower structure of which a larger pressure is applied, as compared with an ordinary full denture, since no regard is paid at all to the form of the occlusal surface thereof.

OBJECT OF THE INVENTION

It is an object of the present invention to provide a solution to the problems the prior art offers.

SUMMARY OF THE INVENTION

According to the present invention, this object is achieved by an artificial tooth having the length of its buccal side substantially equal to that of a natural tooth and the length of its lingual side falling in the range of 4.0 mm to a length shorter than the length of its buccal side by at least 2.5. The basal surface of the artificial tooth is of a concave shape in engagement with a more convex shape than the shape in cross-section of the alveolar ridge. One or two proximal surfaces of the basal surface is or are provided at the substantial center with an occlusally inclined smooth groove having a width of 1.5 to 5.0 mm, a maximum depth of 0.5 to 3.0 mm, and an proximal upper end located away from the highest position. The occlusal surface has a mesiodistal length substantially equal to that of a natural tooth and a $W_2/W_1$ ratio falling in the range of 55 to 95% of that of a natural tooth, wherein $W_1$ is the mesiodistal length and $W_2$ is the buccolingual length.

The artificial tooth according to the present invention has the following advantages over the prior art artificial teeth.

(1) When a partial denture obtained from the present artificial tooth is put in the mouth cavity of a wearer, its appearance is not only comparable to, but is nicer to look at, than that of an ordinary natural tooth, since the length of the lingual side of the artificial tooth is designed to be substantially equal to that of an ordinary natural tooth.

(2) Even when a wearer opens his or her mouth wide, the partial denture does not look strange, since the length of the lingual side of the artificial tooth is designed to be as long as at least 4.0 mm.

(3) One can expect the preparation of dentures to be conducted with improved efficiency, since there is no portion to abut against projections from the metal plate or the retainer located below the lingual side of the artificial tooth, when preparing dentures, and hence interfere with the preparation of dentures because of the fact that the length of the lingual side of the artificial tooth is designed to be shorter than that of the buccal side by at least 2.5 mm.

(4) Dentures having stable strength can be prepared, since a sufficient plate material can be filled in between the basal surface and the alveolar ridge owing to the fact that the basal surface is designed to be of a concave shape in engagement with a more convex shape than the shape in cross-section of the alveolar ridge.

(5) Dentures of improved stability and strength can be prepared, since one or two proximal surfaces of the basal surface is or are previously provided at the substantially lingual center with the occlusally inclined smooth groove having a width of 1.5 to 5.0 mm (sufficient to insert and retain a metal material forming the retainer) and a maximum depth of 0.5 to 3.00 mm (sufficient to produce a retaining effect), the groove serving to precisely define the position at which the leg portions of the retainer often used to prepare partial dentures are to be originally located and to securely retain in place the leg portions of the retainer.

(6) The artificial tooth is nicer to look at, since the leg portions of the retainer are not virtually exposed to view because of the fact that such a groove has its proximal upper end not reaching, or located away from, the highest position of the artificial tooth.

(7) Unlike full dentures, it is possible to prevent a large force from being applied to partial dentures alone at the time when they are prepared, since the masticatory surface of the artificial tooth has a mesiodistal length substantially equal to that of a natural tooth, and a $W_2$ to $W_1$ ratio falling in the range of 55 to 95% of that of a natural tooth, so that an increased play is assured on the masticatory surface during occlusion.

As mentioned above, the artificial teeth according to the present invention have the combined advantages of saving the labor required for the preparation of dentures, improving the appearance of dentures, and assuring a satisfactory mastication effect in use. Further, if the basal surface is bent to a concave shape to increase its surface area, then it provides an increased area of contact with the plate, thus making it possible to prepare dentures of improved stability. Thus, the present invention is of great value.

BRIEF DESCRIPTION OF THE INVENTION

The present invention will now be explained in further detail with reference to the accompanying drawings, which are given by way of example alone, and in which:

FIG. 1 is a perspective view of one embodiment of the artificial tooth for the first molar teeth of the upper jaw, FIG. 2 is a plan view of that embodiment, FIG. 3 is a view, sectioned buccolingually, of the central portion of the occlusal surface of the artificial tooth shown in FIG. 1, FIG. 4 is a view, mesiodistally sectioned, of the central portion of the occlusal surface of the artificial tooth shown in FIG. 1, FIG. 5 is a perspective view of one embodiment of the artificial tooth for the first premolar tooth of the lower jaw, FIG. 6 is a view, mesiodistally sectioned, of the central portion of the occlusal surface of a partial denture prepared with the present artificial tooth of FIG. 1 and a retainer, and FIG. 7 is a side view of one example of a conventional artificial tooth.

DETAILED DESCRIPTION OF THE PRESENTLY PREFERRED EMBODIMENT

Figure 1:
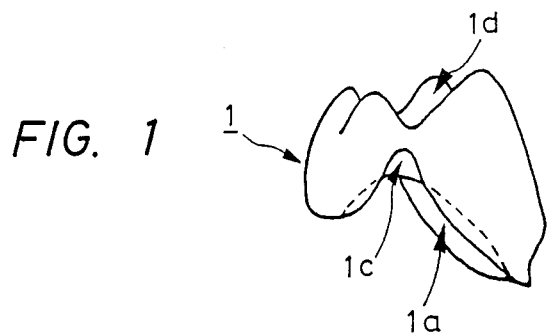
Figure 2:
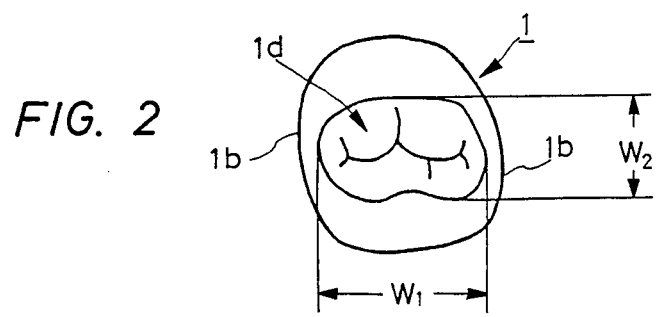
Figure 3:
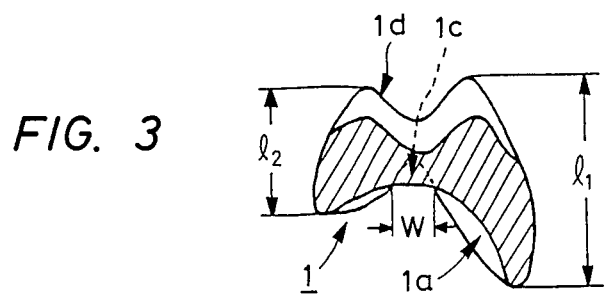
Figure 4:
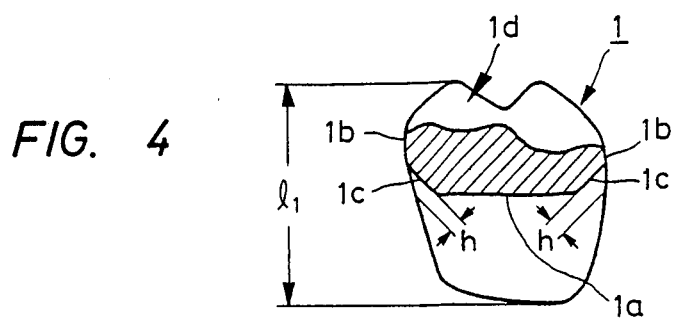

Referring to FIGS. 1 to 5 of the drawings, an artificial tooth according to the present invention, shown generally at 1, is formed of a porcelain or synthetic resin material. The length $l_1$ of the buccal side is substantially equal to that of the buccal side of a natural tooth, and the length $l_2$ of a lingual side is in the range of 4.0 mm or more to a length shorter than the buccal side's length $l_1$ by 2.5 mm or more. A basal surface 1a is of a concave form in coincidence with a more convex form than the form in cross-section of the alveolar ridge. The basal surface 1a is provided on a substantially buccolingual center portion of one or two proximal surfaces with an occlusally inclined smooth groove 1c having a width w of 1.5 to 5.0 mm, a maximum depth h of 0.5 to 3.0 mm, and an proximal upper end not reaching the highest position 1b. An occlusal surface 1d has a mesiodistal lenght $W_1$ substantially equal to that of a natural tooth, and the occlusal surface is designed to have a $W_2$ to $W_1$ ratio falling in the range of 55 to 95% of that of a natural teeth, wherein $W_1$ is the mesiodistal length and $W_2$ is the buccolingual length.

When the basal surface 1a of the artificial tooth of such a structure is mesiodistally bent into a concave shape, its surface area defines an increased area of contact with a plate material to be described later, thus making it possible to prepare a denture of improved stability.

Referring to FIG. 6, reference numeral 2 stands for a retainer formed of a metal material and usually called the clasp. The leg portions of the retainer 2 are inserted along the groove 1c formed in the proximal surfaces of the artificial tooth 1, and they a located below the basal surface 1a of the artificial tooth 1. Reference numeral 3 denotes a plate material formed of a synthetic resin which is colored in accord with the color tone of the alveolar ridge of a wearer.

In what follows, the preparation of a partial denture with the present artificial tooth of such a structure will be explained.

An artificial tooth of a size, form, and color tone which is as accommodative to a lost tooth of a patient as possible is first selected from among a set of artificial teeth according to the present invention. Then, the retainer 2 to be in engagement with the remaining tooth is made on a gypsum model prepared by an impression taken out of the mouth cavity of the patient, and the retainer 2 is positioned such that the base ends of the leg portions thereof are inserted into the groove 1c of the artificial tooth according to the present invention. In this case, the tooth 1 and the retainer 2 are stably held with respect to each other, since the groove 1c in the tooth 1 is designed to have its width w substantially equal to the average width of the leg portions of the retainer 2, and the groove is adapted to firmly retain the leg portions of the retainer 2 at its maximum depth h portion with no gap being formed therebetween. As mentioned above, the groove 1c formed in the artificial tooth 1 of the present invention is such that its width w is substantially equal to the average width of the leg portions of the retainer 2. Thus, the leg portions of the retainer 2 may project slightly widthwise from the groove 1c. In this case, they may be cut according to the width w of the groove 1c. After the retainer 2 is positioned with respect to the artificial tooth 1 in this manner, wax corresponding to the alveolus portion is filled in between the basal surface 1a of the artificial tooth 1 and the portion, corresponding to the lost tooth, of the gypsum model prepared by the impression taken out of the mouth cavity of the patient, and wax corresponding to the gingival portion is formed on the required portion to make a wax denture. In a flask, the wax denture is then invested in a gypsum investment. Afterwards, the gypsum investment having the wax denture invested therein is heated by immersion in warm water to cast off the wax, thereby defining a space for filling the plate material 3. Filled in that space is the plate material 3, which is in turn heated under pressure for polymerization. Finally, the gypsum investment is broken to obtain a partial denture having the artificial tooth 1 and the retainer 2 fixed to each other by the polymerized plate material 3.

It is to be understood that, whilst the present invention has been described with reference to a specific embodiment, many modifications and changes may be made thereto without departing from the scope as defined in the appended claims.

We claim:

1. An artificial tooth having:
   (a) the length of its buccal side substantially equal to that of a natural tooth;
   (b) the length of its lingual side in the range of 4.0 mm to a length shorter than the length of its buccal side by at least 2.5 mm;
   (c) a basal surface that is of a concave shape in engagement with a more convex shape than the shape in cross-section of the alveolar ridge;
   (d) one or two proximal surfaces of the basal surface provided at the substantial center with an occlusally inclined smooth groove having a width of 1.5 to 5.0 mm, a maximum depth of 0.5 to 3.0 mm, and a proximal upper end located away from the highest position; and
   (e) an occlusal surface that has a mesiodistal length substantially equal to that of a natural tooth and a $W_2/W_1$ ratio falling in the range of 55 to 95% of that of a natural tooth, wherein $W_1$ is the mesiodistal length and $W_2$ is the buccolingual length.

2. An artificial tooth as defined in claim 1, which is formed of a porcelain material.

3. An artificial tooth as defined in claim 1, which is formed of a synthetic resin.

4. An artificial tooth as defined in any one of claims 1 to 3, in which the basal surface thereof is mesiodistaly bent into a concave shape.

* * * * *